United States Patent
Okakura et al.

(10) Patent No.: US 9,181,537 B2
(45) Date of Patent: Nov. 10, 2015

(54) CELLULASE PREPARATION COMPRISING ENDOGLUCANASES DERIVED FROM TWO DIFFERENT TYPES OF MICROORGANISMS

(75) Inventors: Kaoru Okakura, Odawara (JP); Koichiro Murashima, Odawara (JP)

(73) Assignee: MEIJI SEIKA PHARMA CO., LTD., Tokyo (JP)

( * ) Notice: Subject to any disclaimer, the term of this patent is extended or adjusted under 35 U.S.C. 154(b) by 73 days.

(21) Appl. No.: 13/381,049

(22) PCT Filed: Jul. 1, 2010

(86) PCT No.: PCT/JP2010/061263
§ 371 (c)(1),
(2), (4) Date: Dec. 27, 2011

(87) PCT Pub. No.: WO2011/002063
PCT Pub. Date: Jan. 6, 2011

(65) Prior Publication Data
US 2012/0100578 A1 Apr. 26, 2012

(30) Foreign Application Priority Data
Jul. 3, 2009 (JP) .................................. 2009-159109

(51) Int. Cl.
| | |
|---|---|
| *C12P 19/00* | (2006.01) |
| *C12N 9/42* | (2006.01) |
| *C12P 19/14* | (2006.01) |
| *C12P 19/02* | (2006.01) |
| *D06M 16/00* | (2006.01) |

(52) U.S. Cl.
CPC ............... *C12N 9/2437* (2013.01); *C12P 19/02* (2013.01); *C12P 19/14* (2013.01); *C12Y 302/01004* (2013.01); *D06M 16/003* (2013.01)

(58) Field of Classification Search
None
See application file for complete search history.

(56) References Cited

U.S. PATENT DOCUMENTS

| | | | | |
|---|---|---|---|---|
| 5,989,899 | A  * | 11/1999 | Bower et al. ................... | 435/263 |
| 6,261,828 | B1 | 7/2001 | Lund | |
| 6,277,596 | B1 | 8/2001 | Watanabe et al. | |
| 8,257,955 | B2 * | 9/2012 | Moriya et al. ................. | 435/209 |
| 2006/0110812 | A1 | 5/2006 | O'Neal Ingram et al. | |
| 2007/0099265 | A1 | 5/2007 | Watanabe | |
| 2007/0111278 | A1 | 5/2007 | Koga et al. | |

(Continued)

FOREIGN PATENT DOCUMENTS

| | | |
|---|---|---|
| CN | 1232506 | 10/1999 |
| CN | 1890367 | 1/2007 |

(Continued)

OTHER PUBLICATIONS

Friedberg, Brief. Bioinformatics (2006) 7: 225-242).*

(Continued)

*Primary Examiner* — Robert Mondesi
*Assistant Examiner* — Thomas J Visone
(74) *Attorney, Agent, or Firm* — Sughrue Mion, PLLC (57) ABSTRACT

By having a cellulase preparation comprising at least a certain amount of endoglucanases derived from two different types of microorganisms, the cellulase preparation can be provided with a higher activity and a wider pH property than those of cellulase preparations each containing one of the endoglucanases alone. Moreover, by introducing and expressing simultaneously two different types of cellulase genes in a single host cell, a cellulase preparation having a high activity and a wide pH property can be produced easily.

7 Claims, 1 Drawing Sheet

(56) References Cited

U.S. PATENT DOCUMENTS

| | | |
|---|---|---|
| 2010/0098807 A1 | 4/2010 | Moriya et al. |
| 2010/0136667 A1* | 6/2010 | Ding et al. ............... 435/277 |
| 2010/0143967 A1 | 6/2010 | McFarland |
| 2011/0165635 A1 | 7/2011 | Copenhaver et al. |

FOREIGN PATENT DOCUMENTS

| | | | |
|---|---|---|---|
| EP | 0 307 564 B1 | 3/1989 | |
| JP | 9-500667 A | 1/1997 | |
| JP | 2004-501636 A | 1/2004 | |
| WO | WO 95/02675 A | 1/1995 | |
| WO | 9718286 | 5/1997 | |
| WO | WO 98/54332 A1 | 12/1998 | |
| WO | 0200858 | 1/2002 | |
| WO | WO 2005/054475 A1 | 6/2005 | |
| WO | WO 2008/111613 A1 | 9/2008 | |
| WO | 2008140749 | 11/2008 | |
| WO | WO 2008/153903 | * 12/2008 | ............ C12N 1/15 |
| WO | 2009132008 | 10/2009 | |

OTHER PUBLICATIONS

Thorton et al., Nature structural biology, structural genomics supplement, Nov. 2000, pp. 991-994).*

Guo et al., PNAS 2004 (101)25,9205-9210.*

Sandgren et al (Prog. Biophysc. Mol. Biol., 89: 246-291 (2005).*

Vlasenko et al., Biores. Technol., 101:2405-2411 (2010).*

Karlsson et al., J. Biotechnol., 99:63-78 (2002).*

English translation of International Preliminary Report on Patentability for PCT/JP2010/061263 dated Feb. 23, 2012.

Murashima et al., "Synergistic Effects on Crystalline Cellulose Degradation between Cellulosomal cellulases from Chlostridium Cellulovorans", J. of Bacteriology, American Society for Microbiology, 184(18):5088-5095 (2002).

Database Geneseq, "A cellulase enzyme designated SCE-3.", Abstract No. XP002687636 (Database Accession No. AAW97208), dated May 7, 1999.

Database Geneseq, "*P. pinophilum* modified endoglucanase ppcE SEQ 30.", Abstract No. XP002687637 (Database Accession No. ATN95903), dated Nov. 27, 2008.

Database Geneseq, "*S. coccosporum* endoglucanase STCE1.", Abstract No. XP002687638 (Database Accession No. AEA35080), dated Aug. 25, 2005.

Vlasenko et al., "Substrate specificity of family 5, 6, 7, 9, 12, and 45 endoglucanases", Bioresource Technology, 101(7):2405-2411 (2010).

* cited by examiner

SEQUENCE LISTING

<160> NUMBER OF SEQ ID NOS: 6

<210> SEQ ID NO 1
<211> LENGTH: 1194
<212> TYPE: DNA
<213> ORGANISM: Trichoderma viride
<220> FEATURE:
<221> NAME/KEY: CDS
<222> LOCATION: (1)..(1191)

<400> SEQUENCE: 1

| | | | | | | | | | | | | | | | | |
|---|---|---|---|---|---|---|---|---|---|---|---|---|---|---|---|---|
| caa | cag | act | gtc | tgg | gga | cag | tgt | gga | ggt | att | ggt | tgg | agc | gga | cct | 48 |
| Gln | Gln | Thr | Val | Trp | Gly | Gln | Cys | Gly | Gly | Ile | Gly | Trp | Ser | Gly | Pro | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| acg | agt | tgt | gct | cct | gga | tca | gct | tgt | tct | act | ctc | aat | cct | tat | tat | 96 |
| Thr | Ser | Cys | Ala | Pro | Gly | Ser | Ala | Cys | Ser | Thr | Leu | Asn | Pro | Tyr | Tyr | |
| | | | 20 | | | | | 25 | | | | | 30 | | | |

| | | | | | | | | | | | | | | | | |
|---|---|---|---|---|---|---|---|---|---|---|---|---|---|---|---|---|
| gcg | caa | tgc | att | ccg | ggg | gcc | act | agt | atc | acc | acc | tcg | acc | cga | ccc | 144 |
| Ala | Gln | Cys | Ile | Pro | Gly | Ala | Thr | Ser | Ile | Thr | Thr | Ser | Thr | Arg | Pro | |
| | | 35 | | | | | 40 | | | | | 45 | | | | |

| | | | | | | | | | | | | | | | | |
|---|---|---|---|---|---|---|---|---|---|---|---|---|---|---|---|---|
| ccc | tcg | ggt | cca | acc | acc | acc | aga | gcc | acc | tca | acg | acc | tca | tct | | 192 |
| Pro | Ser | Gly | Pro | Thr | Thr | Thr | Arg | Ala | Thr | Ser | Thr | Thr | Ser | Ser | | |
| 50 | | | | | 55 | | | | | 60 | | | | | | |

| | | | | | | | | | | | | | | | | |
|---|---|---|---|---|---|---|---|---|---|---|---|---|---|---|---|---|
| ccg | cca | ccg | acc | agc | tct | gga | gtt | cga | ttt | gct | ggc | gtt | aac | atc | gcg | 240 |
| Pro | Pro | Pro | Thr | Ser | Ser | Gly | Val | Arg | Phe | Ala | Gly | Val | Asn | Ile | Ala | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| ggc | ttt | gac | ttc | gga | tgt | acc | aca | gat | ggc | act | tgc | gtt | aca | tcg | aag | 288 |
| Gly | Phe | Asp | Phe | Gly | Cys | Thr | Thr | Asp | Gly | Thr | Cys | Val | Thr | Ser | Lys | |
| | | | | 85 | | | | | 90 | | | | | 95 | | |

| | | | | | | | | | | | | | | | | |
|---|---|---|---|---|---|---|---|---|---|---|---|---|---|---|---|---|
| gtt | tat | cct | ccg | ttg | aag | aac | ttc | act | ggg | gca | aac | aac | tac | ccg | gac | 336 |
| Val | Tyr | Pro | Pro | Leu | Lys | Asn | Phe | Thr | Gly | Ala | Asn | Asn | Tyr | Pro | Asp | |
| | | | 100 | | | | | 105 | | | | | 110 | | | |

| | | | | | | | | | | | | | | | | |
|---|---|---|---|---|---|---|---|---|---|---|---|---|---|---|---|---|
| ggt | atc | ggc | cag | atg | cag | cac | ttc | gtc | aac | gat | gat | ggg | atg | act | att | 384 |
| Gly | Ile | Gly | Gln | Met | Gln | His | Phe | Val | Asn | Asp | Asp | Gly | Met | Thr | Ile | |
| | | 115 | | | | | 120 | | | | | 125 | | | | |

| | | | | | | | | | | | | | | | | |
|---|---|---|---|---|---|---|---|---|---|---|---|---|---|---|---|---|
| ttc | cgc | cta | ccc | gtc | gga | tgg | cag | tac | ctc | gta | aac | aac | aat | ctg | ggt | 432 |
| Phe | Arg | Leu | Pro | Val | Gly | Trp | Gln | Tyr | Leu | Val | Asn | Asn | Asn | Leu | Gly | |
| | 130 | | | | | 135 | | | | | 140 | | | | | |

| | | | | | | | | | | | | | | | | |
|---|---|---|---|---|---|---|---|---|---|---|---|---|---|---|---|---|
| gga | act | ctc | gat | tcc | acc | agt | atc | tcg | aag | tat | gat | cag | ctc | gtt | cag | 480 |
| Gly | Thr | Leu | Asp | Ser | Thr | Ser | Ile | Ser | Lys | Tyr | Asp | Gln | Leu | Val | Gln | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| ggg | tgc | ctg | tct | ctc | ggt | gta | tac | tgc | atc | atc | gac | atc | cac | aat | tat | 528 |
| Gly | Cys | Leu | Ser | Leu | Gly | Val | Tyr | Cys | Ile | Ile | Asp | Ile | His | Asn | Tyr | |
| | | | | 165 | | | | | 170 | | | | | 175 | | |

| | | | | | | | | | | | | | | | | |
|---|---|---|---|---|---|---|---|---|---|---|---|---|---|---|---|---|
| gct | cga | tgg | aac | ggt | gga | atc | att | ggc | cag | gga | ggc | cct | aca | aat | gcc | 576 |
| Ala | Arg | Trp | Asn | Gly | Gly | Ile | Ile | Gly | Gln | Gly | Gly | Pro | Thr | Asn | Ala | |
| | | | 180 | | | | | 185 | | | | | 190 | | | |

| | | | | | | | | | | | | | | | | |
|---|---|---|---|---|---|---|---|---|---|---|---|---|---|---|---|---|
| cag | ttt | acc | agt | ctt | tgg | tcg | cag | ttg | gca | tcg | aag | tac | gcg | tct | cag | 624 |
| Gln | Phe | Thr | Ser | Leu | Trp | Ser | Gln | Leu | Ala | Ser | Lys | Tyr | Ala | Ser | Gln | |
| | | 195 | | | | | 200 | | | | | 205 | | | | |

| | | | | | | | | | | | | | | | | |
|---|---|---|---|---|---|---|---|---|---|---|---|---|---|---|---|---|
| tcg | agg | gtg | tgg | ttc | gga | ata | atg | aat | gag | ccc | cac | gac | gtg | aac | atc | 672 |
| Ser | Arg | Val | Trp | Phe | Gly | Ile | Met | Asn | Glu | Pro | His | Asp | Val | Asn | Ile | |
| | 210 | | | | | 215 | | | | | 220 | | | | | |

| | | | | | | | | | | | | | | | | |
|---|---|---|---|---|---|---|---|---|---|---|---|---|---|---|---|---|
| aac | act | tgg | gct | gcc | acg | gtt | caa | gag | gtc | gtc | act | gca | atc | cgc | aac | 720 |
| Asn | Thr | Trp | Ala | Ala | Thr | Val | Gln | Glu | Val | Val | Thr | Ala | Ile | Arg | Asn | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| gcc | ggt | gct | acg | tcg | caa | tac | att | tct | ctg | cct | gga | aat | gat | tat | caa | 768 |
| Ala | Gly | Ala | Thr | Ser | Gln | Tyr | Ile | Ser | Leu | Pro | Gly | Asn | Asp | Tyr | Gln | |
| | | | | 245 | | | | | 250 | | | | | 255 | | |

-continued

| | | |
|---|---|---|
| tct gcg gca gct ttt att tcc gat ggc agt gca gcc gcc ctg tct cag<br>Ser Ala Ala Ala Phe Ile Ser Asp Gly Ser Ala Ala Ala Leu Ser Gln<br>260                            265                        270 | 816 |
| gta acg aac cct gat gga tca aca acg aat cta atc ttc gat gtc cac<br>Val Thr Asn Pro Asp Gly Ser Thr Thr Asn Leu Ile Phe Asp Val His<br>        275                          280                          285 | 864 |
| aag tac tta gac tcg gac aac tcc ggt act cac gcc gaa tgc act aca<br>Lys Tyr Leu Asp Ser Asp Asn Ser Gly Thr His Ala Glu Cys Thr Thr<br>290                            295                        300 | 912 |
| aac aac atc gac ggc gcc ttt gct cct ctc gcc act tgg ctt cga cag<br>Asn Asn Ile Asp Gly Ala Phe Ala Pro Leu Ala Thr Trp Leu Arg Gln<br>305                            310                            315                       320 | 960 |
| aac aac cgc cag gct att ctg acg gaa acc ggc ggt ggc aat gtt cag<br>Asn Asn Arg Gln Ala Ile Leu Thr Glu Thr Gly Gly Gly Asn Val Gln<br>                      325                          330                        335 | 1008 |
| tcc tgc atc caa gat ttg tgc caa cag atc cag tac ctc aac cag aac<br>Ser Cys Ile Gln Asp Leu Cys Gln Gln Ile Gln Tyr Leu Asn Gln Asn<br>340                            345                        350 | 1056 |
| tca gat gtc tat ctt ggc tat gct ggc tgg ggt gcc ggt tca ttt gat<br>Ser Asp Val Tyr Leu Gly Tyr Ala Gly Trp Gly Ala Gly Ser Phe Asp<br>                      355                          360                        365 | 1104 |
| agc act tat att ctg acg gaa acg cct act gga agc ggt aac tcg tgg<br>Ser Thr Tyr Ile Leu Thr Glu Thr Pro Thr Gly Ser Gly Asn Ser Trp<br>370                            375                        380 | 1152 |
| acg gac aca tcc cta gtt agc tcg tgt ctc gcc agg aag taa<br>Thr Asp Thr Ser Leu Val Ser Ser Cys Leu Ala Arg Lys<br>385                            390                        395 | 1194 |

<210> SEQ ID NO 2
<211> LENGTH: 397
<212> TYPE: PRT
<213> ORGANISM: Trichoderma viride

<400> SEQUENCE: 2

Gln Gln Thr Val Trp Gly Gln Cys Gly Gly Ile Gly Trp Ser Gly Pro
1                 5                    10                  15

Thr Ser Cys Ala Pro Gly Ser Ala Cys Ser Thr Leu Asn Pro Tyr Tyr
                20                    25                  30

Ala Gln Cys Ile Pro Gly Ala Thr Ser Ile Thr Thr Ser Thr Arg Pro
                35                    40                  45

Pro Ser Gly Pro Thr Thr Thr Thr Arg Ala Thr Ser Thr Ser Ser
50                      55                    60

Pro Pro Thr Ser Ser Gly Val Arg Phe Ala Gly Val Asn Ile Ala
65                    70                    75                  80

Gly Phe Asp Phe Gly Cys Thr Thr Asp Gly Thr Cys Val Thr Ser Lys
                85                    90                  95

Val Tyr Pro Pro Leu Lys Asn Phe Thr Gly Ala Asn Asn Tyr Pro Asp
                100                    105                  110

Gly Ile Gly Gln Met Gln His Phe Val Asn Asp Asp Gly Met Thr Ile
                115                    120                  125

Phe Arg Leu Pro Val Gly Trp Gln Tyr Leu Val Asn Asn Asn Leu Gly
130                      135                    140

Gly Thr Leu Asp Ser Thr Ser Ile Ser Lys Tyr Asp Gln Leu Val Gln
145                      150                    155                  160

Gly Cys Leu Ser Leu Gly Val Tyr Cys Ile Ile Asp Ile His Asn Tyr
                165                    170                  175

Ala Arg Trp Asn Gly Gly Ile Ile Gly Gln Gly Gly Pro Thr Asn Ala
                180                    185                  190

```
Gln Phe Thr Ser Leu Trp Ser Gln Leu Ala Ser Lys Tyr Ala Ser Gln
            195                 200                 205

Ser Arg Val Trp Phe Gly Ile Met Asn Glu Pro His Asp Val Asn Ile
    210                 215                 220

Asn Thr Trp Ala Ala Thr Val Gln Glu Val Val Thr Ala Ile Arg Asn
225                 230                 235                 240

Ala Gly Ala Thr Ser Gln Tyr Ile Ser Leu Pro Gly Asn Asp Tyr Gln
                245                 250                 255

Ser Ala Ala Ala Phe Ile Ser Asp Gly Ser Ala Ala Ala Leu Ser Gln
                260                 265                 270

Val Thr Asn Pro Asp Gly Ser Thr Thr Asn Leu Ile Phe Asp Val His
            275                 280                 285

Lys Tyr Leu Asp Ser Asp Asn Ser Gly Thr His Ala Glu Cys Thr Thr
            290                 295                 300

Asn Asn Ile Asp Gly Ala Phe Ala Pro Leu Ala Thr Trp Leu Arg Gln
305                 310                 315                 320

Asn Asn Arg Gln Ala Ile Leu Thr Glu Thr Gly Gly Gly Asn Val Gln
                325                 330                 335

Ser Cys Ile Gln Asp Leu Cys Gln Gln Ile Gln Tyr Leu Asn Gln Asn
                340                 345                 350

Ser Asp Val Tyr Leu Gly Tyr Ala Gly Trp Gly Ala Gly Ser Phe Asp
            355                 360                 365

Ser Thr Tyr Ile Leu Thr Glu Thr Pro Thr Gly Ser Gly Asn Ser Trp
            370                 375                 380

Thr Asp Thr Ser Leu Val Ser Ser Cys Leu Ala Arg Lys
385                 390                 395

<210> SEQ ID NO 3
<211> LENGTH: 666
<212> TYPE: DNA
<213> ORGANISM: Penicillium pinophilum
<220> FEATURE:
<221> NAME/KEY: CDS
<222> LOCATION: (1)..(663)

<400> SEQUENCE: 3 cag cag agc ctg tgc agc cag tac agc agc tac acc agc ggc cag tac    48
Gln Gln Ser Leu Cys Ser Gln Tyr Ser Ser Tyr Thr Ser Gly Gln Tyr
1               5                   10                  15 agc gtc aac aac aac ctg tgg ggc gag agc agc ggc agc ggc agc cag    96
Ser Val Asn Asn Asn Leu Trp Gly Glu Ser Ser Gly Ser Gly Ser Gln
                20                  25                  30 tgc acc tac gtc aac agc atc agc agc agc ggc gtc agc tgg agc acc   144
Cys Thr Tyr Val Asn Ser Ile Ser Ser Ser Gly Val Ser Trp Ser Thr
            35                  40                  45 acc tgg aac tgg agc ggc ggc agc acc agc gtc aag agc tac gcc aac   192
Thr Trp Asn Trp Ser Gly Gly Ser Thr Ser Val Lys Ser Tyr Ala Asn
        50                  55                  60 agc cag ctg agc ggc ctg acc aag aag ctg gtc agc aac ctg cag agc   240
Ser Gln Leu Ser Gly Leu Thr Lys Lys Leu Val Ser Asn Leu Gln Ser
65                  70                  75                  80 atc ccc acc agc gtc cag tgg agc tac agc aac acc aac atc gtc gcc   288
Ile Pro Thr Ser Val Gln Trp Ser Tyr Ser Asn Thr Asn Ile Val Ala
                85                  90                  95 gac gtc agc tac gac ctg ttc acc gcc gcc gac atc aac cac gtc acc   336
Asp Val Ser Tyr Asp Leu Phe Thr Ala Ala Asp Ile Asn His Val Thr
            100                 105                 110
```

|  |  |
|---|---|
| tac agc ggc gac tac gag ctg atg atc tgg ctg ggc aag tac ggc ggc<br>Tyr Ser Gly Asp Tyr Glu Leu Met Ile Trp Leu Gly Lys Tyr Gly Gly<br>              115                            120                          125 | 384 |
| gcc cag ccc ctg ggc agc cag atc ggc acc gcc aac gtc ggc ggc gcc<br>Ala Gln Pro Leu Gly Ser Gln Ile Gly Thr Ala Asn Val Gly Gly Ala<br>130                            135                          140 | 432 |
| acc tgg cag ctg tgg tac ggc gtc aac ggc agc cag aag acc tac agc<br>Thr Trp Gln Leu Trp Tyr Gly Val Asn Gly Ser Gln Lys Thr Tyr Ser<br>145                          150                        155                        160 | 480 |
| ttc gtc gcc agc agc cag acc acc agc tgg aac ggc gac atc ctg cag<br>Phe Val Ala Ser Ser Gln Thr Thr Ser Trp Asn Gly Asp Ile Leu Gln<br>              165                          170                          175 | 528 |
| ttc ttc aag tac ctg cag agc aac cag ggc ttc ccc gcc agc agc cag<br>Phe Phe Lys Tyr Leu Gln Ser Asn Gln Gly Phe Pro Ala Ser Ser Gln<br>                       180                          185                          190 | 576 |
| tac ctg atc gac ctg cag ttc ggc acc gag ccc ttc acc ggc agc cag<br>Tyr Leu Ile Asp Leu Gln Phe Gly Thr Glu Pro Phe Thr Gly Ser Gln<br>              195                          200                          205 | 624 |
| acc acc ctg acc gtc aac cac tgg agc gcc agc gtc aac tag<br>Thr Thr Leu Thr Val Asn His Trp Ser Ala Ser Val Asn<br>210                          215                          220 | 666 |

```
<210> SEQ ID NO 4
<211> LENGTH: 221
<212> TYPE: PRT
<213> ORGANISM: Penicillium pinophilum

<400> SEQUENCE: 4
```

Gln Gln Ser Leu Cys Ser Gln Tyr Ser Ser Tyr Thr Ser Gly Gln Tyr
1               5                   10                  15

Ser Val Asn Asn Asn Leu Trp Gly Glu Ser Ser Gly Ser Gly Ser Gln
                20                  25                  30

Cys Thr Tyr Val Asn Ser Ile Ser Ser Ser Gly Val Ser Trp Ser Thr
            35                  40                  45

Thr Trp Asn Trp Ser Gly Gly Ser Thr Ser Val Lys Ser Tyr Ala Asn
    50                  55                  60

Ser Gln Leu Ser Gly Leu Thr Lys Lys Leu Val Ser Asn Leu Gln Ser
65                  70                  75                  80

Ile Pro Thr Ser Val Gln Trp Ser Tyr Ser Asn Thr Asn Ile Val Ala
                85                  90                  95

Asp Val Ser Tyr Asp Leu Phe Thr Ala Ala Asp Ile Asn His Val Thr
            100                 105                 110

Tyr Ser Gly Asp Tyr Glu Leu Met Ile Trp Leu Gly Lys Tyr Gly Gly
        115                 120                 125

Ala Gln Pro Leu Gly Ser Gln Ile Gly Thr Ala Asn Val Gly Gly Ala
130                 135                 140

Thr Trp Gln Leu Trp Tyr Gly Val Asn Gly Ser Gln Lys Thr Tyr Ser
145                 150                 155                 160

Phe Val Ala Ser Ser Gln Thr Thr Ser Trp Asn Gly Asp Ile Leu Gln
                165                 170                 175

Phe Phe Lys Tyr Leu Gln Ser Asn Gln Gly Phe Pro Ala Ser Ser Gln
            180                 185                 190

Tyr Leu Ile Asp Leu Gln Phe Gly Thr Glu Pro Phe Thr Gly Ser Gln
        195                 200                 205

Thr Thr Leu Thr Val Asn His Trp Ser Ala Ser Val Asn
210                 215                 220

```
<210> SEQ ID NO 5
<211> LENGTH: 888
<212> TYPE: DNA
<213> ORGANISM: Staphylotrichum cocosporum
<220> FEATURE:
<221> NAME/KEY: CDS
<222> LOCATION: (1)..(885)

<400> SEQUENCE: 5 gcc gat ggc aag tcg acc cgc tac tgg gac tgt tgc aag ccg tcg tgc       48
Ala Asp Gly Lys Ser Thr Arg Tyr Trp Asp Cys Cys Lys Pro Ser Cys
1               5                   10                  15 tcg tgg ccc ggc aag gcc tcg gtg aac cag ccc gtc ttc gcc tgc agc       96
Ser Trp Pro Gly Lys Ala Ser Val Asn Gln Pro Val Phe Ala Cys Ser
            20                  25                  30 gcc aac ttc cag cgc atc agc gac ccc aac gtc aag tcg ggc tgc gac      144
Ala Asn Phe Gln Arg Ile Ser Asp Pro Asn Val Lys Ser Gly Cys Asp
        35                  40                  45 ggc ggc tcc gcc tac gcc tgc gcc gac cag acc ccg tgg gcc gtc aac      192
Gly Gly Ser Ala Tyr Ala Cys Ala Asp Gln Thr Pro Trp Ala Val Asn
    50                  55                  60 gac aac ttc tcg tac ggc ttc gcc gcc acg tcc atc tcg ggc ggc aac      240
Asp Asn Phe Ser Tyr Gly Phe Ala Ala Thr Ser Ile Ser Gly Gly Asn
65                  70                  75                  80 gag gcc tcg tgg tgc tgt ggc tgc tac gag ctg acc ttc acc tcg ggc      288
Glu Ala Ser Trp Cys Cys Gly Cys Tyr Glu Leu Thr Phe Thr Ser Gly
                85                  90                  95 ccc gtc gct ggc aag acc atg gtt gtc cag tcc acc tcg acc ggc ggc      336
Pro Val Ala Gly Lys Thr Met Val Val Gln Ser Thr Ser Thr Gly Gly
            100                 105                 110 gac ctc ggc acc aac cac ttc gac ctg gcc atg ccc ggt ggt ggt gtc      384
Asp Leu Gly Thr Asn His Phe Asp Leu Ala Met Pro Gly Gly Gly Val
        115                 120                 125 ggc atc ttc gac ggc tgc tcg ccc cag ttc ggc ggc ctc gcc ggc gac      432
Gly Ile Phe Asp Gly Cys Ser Pro Gln Phe Gly Gly Leu Ala Gly Asp
    130                 135                 140 cgc tac ggc ggc gtc tcg tcg cgc agc cag tgc gac tcg ttc ccc gcc      480
Arg Tyr Gly Gly Val Ser Ser Arg Ser Gln Cys Asp Ser Phe Pro Ala
145                 150                 155                 160 gcc ctc aag ccc ggc tgc tac tgg cgc ttc gac tgg ttc aag aac gcc      528
Ala Leu Lys Pro Gly Cys Tyr Trp Arg Phe Asp Trp Phe Lys Asn Ala
                165                 170                 175 gac aac ccg acc ttc acc ttc cgc cag gtc cag tgc ccg tcg gag ctc      576
Asp Asn Pro Thr Phe Thr Phe Arg Gln Val Gln Cys Pro Ser Glu Leu
            180                 185                 190 gtc gcc cgc acc ggc tgc cgc cgc aac gac gac ggc aac ttc ccc gtc      624
Val Ala Arg Thr Gly Cys Arg Arg Asn Asp Asp Gly Asn Phe Pro Val
        195                 200                 205 ttc acc cct ccc tcg ggc ggt cag tcc tcc tcg tct tcc tcc tcc agc      672
Phe Thr Pro Pro Ser Gly Gly Gln Ser Ser Ser Ser Ser Ser Ser Ser
    210                 215                 220 agc gcc aag ccc acc tcc acc tcc acc tcg acc acc tcc acc aag gct      720
Ser Ala Lys Pro Thr Ser Thr Ser Thr Ser Thr Thr Ser Thr Lys Ala
225                 230                 235                 240 acc tcc acc acc tcg acc gcc tcc agc cag acc tcg tcg tcc acc ggc      768
Thr Ser Thr Thr Ser Thr Ala Ser Ser Gln Thr Ser Ser Ser Thr Gly
                245                 250                 255 ggc ggc tgc gcc gcc cag cgc tgg gcg cag tgc ggc ggc atc ggg ttc      816
Gly Gly Cys Ala Ala Gln Arg Trp Ala Gln Cys Gly Gly Ile Gly Phe
            260                 265                 270
```

```
tcg ggc tgc acc acg tgc gtc agc ggc acc acc tgc aac aag cag aac    864
Ser Gly Cys Thr Thr Cys Val Ser Gly Thr Thr Cys Asn Lys Gln Asn
        275                 280                 285 gac tgg tac tcg cag tgc ctt taa                                    888
Asp Trp Tyr Ser Gln Cys Leu
    290                 295

<210> SEQ ID NO 6
<211> LENGTH: 295
<212> TYPE: PRT
<213> ORGANISM: Staphylotrichum cocosporum

<400> SEQUENCE: 6

Ala Asp Gly Lys Ser Thr Arg Tyr Trp Asp Cys Cys Lys Pro Ser Cys
1               5                   10                  15

Ser Trp Pro Gly Lys Ala Ser Val Asn Gln Pro Val Phe Ala Cys Ser
            20                  25                  30

Ala Asn Phe Gln Arg Ile Ser Asp Pro Asn Val Lys Ser Gly Cys Asp
        35                  40                  45

Gly Gly Ser Ala Tyr Ala Cys Ala Asp Gln Thr Pro Trp Ala Val Asn
    50                  55                  60

Asp Asn Phe Ser Tyr Gly Phe Ala Ala Thr Ser Ile Ser Gly Gly Asn
65                  70                  75                  80

Glu Ala Ser Trp Cys Cys Gly Cys Tyr Glu Leu Thr Phe Thr Ser Gly
                85                  90                  95

Pro Val Ala Gly Lys Thr Met Val Val Gln Ser Thr Ser Thr Gly Gly
            100                 105                 110

Asp Leu Gly Thr Asn His Phe Asp Leu Ala Met Pro Gly Gly Gly Val
        115                 120                 125

Gly Ile Phe Asp Gly Cys Ser Pro Gln Phe Gly Gly Leu Ala Gly Asp
    130                 135                 140

Arg Tyr Gly Gly Val Ser Ser Arg Ser Gln Cys Asp Ser Phe Pro Ala
145                 150                 155                 160

Ala Leu Lys Pro Gly Cys Tyr Trp Arg Phe Asp Trp Phe Lys Asn Ala
                165                 170                 175

Asp Asn Pro Thr Phe Thr Phe Arg Gln Val Gln Cys Pro Ser Glu Leu
            180                 185                 190

Val Ala Arg Thr Gly Cys Arg Arg Asn Asp Asp Gly Asn Phe Pro Val
        195                 200                 205

Phe Thr Pro Pro Ser Gly Gly Gln Ser Ser Ser Ser Ser Ser Ser Ser
    210                 215                 220

Ser Ala Lys Pro Thr Ser Thr Ser Thr Ser Thr Thr Ser Thr Lys Ala
225                 230                 235                 240

Thr Ser Thr Thr Ser Thr Ala Ser Ser Gln Thr Ser Ser Ser Thr Gly
                245                 250                 255

Gly Gly Cys Ala Ala Gln Arg Trp Ala Gln Cys Gly Gly Ile Gly Phe
            260                 265                 270

Ser Gly Cys Thr Thr Cys Val Ser Gly Thr Thr Cys Asn Lys Gln Asn
        275                 280                 285

Asp Trp Tyr Ser Gln Cys Leu
    290                 295
```

CELLULASE PREPARATION COMPRISING ENDOGLUCANASES DERIVED FROM TWO DIFFERENT TYPES OF MICROORGANISMS

CROSS REFERENCE TO RELATED APPLICATIONS

This application is a National Stage of International Application No. PCT/JP2010/061263 filed Jul. 1, 2010, claiming priority based on Japanese Patent Application No. 2009-159109 filed Jul. 3, 2009 the contents of all of which are incorporated herein by reference in their entirety.

TECHNICAL FIELD

The present invention relates to a cellulase preparation comprising endoglucanases derived from two different types of microorganisms, a method for producing the cellulase preparation, and uses of the cellulase preparation.

BACKGROUND ART

Conventionally, a cellulose-containing fiber has been treated with cellulase to impart desired properties to the fiber. For example, in the textile industry, treatment with a cellulase is carried out to improve the touch feel and appearance of a cellulose-containing fiber, or to give a colored cellulose-containing fiber a "stonewashed" appearance providing local variations in color (Patent Literature 1).

Heretofore, in searching for cellulases utilized for such uses, components exhibiting a high activity for a cellulose-containing fiber have been isolated from cellulase composites produced by cellulase-producing fungi such as filamentous fungi. As a result, endoglucanases classified in GH family 5, GH family 12, and GH family 45 have been isolated as cellulases exhibiting a high activity mainly for a cellulose-containing fiber. For example, SCE3 derived from *Trichoderma viride* has been known as an endoglucanase classified in GH family 5 (Patent Literature 2); PPCE derived from *Penicillium pinophilum* has been known as an endoglucanase classified in GH family 12 (Patent Literature 3); STCE derived from *Staphylotrichum cocosporum* has been known as an endoglucanase classified in GH family 45 (Patent Literature 4); and so forth.

In a case where any of these cellulases is commercially produced, generally a transformant obtained by introducing genes encoding the cellulase into a microorganism such as a filamentous fungus is cultured, and a larger amount of the cellulase is expressed as a recombinant enzyme. In this case, the activity of a thus-prepared cellulase preparation for a cellulose-containing fiber depends on the activity of the recombinant cellulase expressed in a large amount. Similarly, the pH property of the cellulase preparation also depends on the properties of the recombinant cellulase expressed in the large amount. For example, in the case of SCE3, the optimum pH is weakly acidic (Patent Literature 2), while, in the case of PPCE, the optimum pH is acidic (Patent Literature 3). Accordingly, cellulase preparations obtained by expressing large amounts of SCE3 and PPCE as recombinant enzymes exhibit the same pH properties as those of SCE3 and PPCE, respectively.

So far, in order to improve the activity of and modify the properties of a cellulase preparation, attempts have been made mainly to search for a novel cellulase exhibiting desired properties and to modify known cellulases through a protein engineering approach. However, to obtain a cellulase exhibiting an activity significantly superior to known cellulases, first, a novel microorganism has to be isolated, which is not easy to do. Further, the possibility that the microorganism or the like produces a cellulase having desired properties is low. In addition, even if mutation is introduced into a known cellulase through a protein engineering approach, it is difficult to drastically modify the properties of the known cellulase. Due to these problems, conventionally and at present, a cellulase preparation having both a high activity and an excellent pH property has yet to be obtained.

CITATION LIST

Patent Literature

[PTL 1] European Patent No. 307564
[PTL 2] International Publication No. WO98/54332
[PTL 3] International Publication No. WO2008/111613
[PTL 4] International Publication No. WO2005/054475

SUMMARY OF INVENTION

Technical Problem

The present invention has been made in view of such circumstances. An object of the present invention is to provide a cellulase preparation having a high activity and an excellent pH property. Another object of the present invention is to provide a method for easily producing such a cellulase preparation.

Solution to Problem

The present inventors have earnestly studied in order to solve the above problems. As a result, it was found out that by producing a cellulase preparation comprising at least certain proportions of endoglucanases derived from two different types of filamentous fungi, a surprisingly higher activity for a cellulose-containing fiber was obtained than cellulase preparations each obtained by expressing one of the endoglucanases alone. Particularly, if a cellulase preparation comprised as main cellulases a combination of SCE3 (classified in GH family 5) derived from *Trichoderma viride* with PPCE (classified in GH family 12) derived from *Penicillium pinophilum*, or a combination of PPCE derived from *Penicillium pinophilum* with STCE (classified in GH family 45) derived from *Staphylotrichum cocosporum*, an activity for a cellulose-containing fiber was significantly increased. Moreover, the pH property of the cellulase preparation obtained as described above shows a wider profile than the cellulase preparations obtained by expressing one of the endoglucanases alone. It was revealed that a combination of the two types of the endoglucanases made it possible to modify the pH property of the cellulase preparation. Further, the present inventors found out that, in production of such a cellulase preparation, if DNAs encoding endoglucanases derived from two different types of microorganisms were introduced and expressed in a single host cell, the ratio of the recombinant endoglucanases to secreted proteins is increased, and a culture supernatant having a high activity was obtained, in comparison with a case where each of the endoglucanases was introduced and expressed in a host cell alone.

Specifically, the present invention relates to a cellulase preparation comprising endoglucanases derived from two different types of microorganisms, a method for producing the cellulase preparation, and uses of the cellulase preparation. More specifically, the present invention provides the followings.

(1) A cellulase preparation comprising endoglucanases derived from two different types of microorganisms.
(2) The cellulase preparation according to (1), wherein the endoglucanases are derived from two different types of filamentous fungi.
(3) The cellulase preparation according to (1), wherein the endoglucanases derived from the two different types of microorganisms are both recombinant proteins.
(4) The cellulase preparation according to anyone of (1) to (3), wherein two main types of the endoglucanases are each contained in an amount of at least 10% by weight of total cellulases.
(5) The cellulase preparation according to (4), wherein the two main types of the endoglucanases are each contained in an amount of at least 20% by weight of the total cellulases.
(6) The cellulase preparation according to any one of (1) to (3), wherein two main types of the endoglucanases are classified in different GH families.
(7) The cellulase preparation according to (6), wherein each of the two main types of the endoglucanases is classified in any of GH family 5, GH family 12, and GH family 45.
(8) The cellulase preparation according to (7), wherein the two main types of the endoglucanases are a combination of any one of the following (a) and (b):
(a) a combination of an endoglucanase classified in GH family 5 with an endoglucanase classified in GH family 12; and
(b) a combination of an endoglucanase classified in GH family 12 with an endoglucanase classified in GH family 45.
(9) The cellulase preparation according to (8), wherein
the endoglucanase classified in GH family 5 is a protein having any one of an amino acid sequence of SEQ ID NO: 2 and the amino acid sequence in which one or more amino acids are deleted, substituted, inserted, or added,
the endoglucanase classified in GH family 12 is a protein having any one of an amino acid sequence of SEQ ID NO: 4 and the amino acid sequence in which one or more amino acids are deleted, substituted, inserted, or added, and
the endoglucanase classified in GH family 45 is a protein having any one of an amino acid sequence of SEQ ID NO: 6 and the amino acid sequence in which one or more amino acids are deleted, substituted, inserted, or added.
(10) A method for producing the cellulase preparation according to (3), the method comprising the step of culturing a transformant obtained by introducing DNAs encoding two types of the endoglucanases into a single host cell.
(11) The method according to (10), wherein the host cell is a filamentous fungus.
(12) A method for producing an improved cellulose-containing fiber, the method comprising the step of bringing a cellulose-containing fiber into contact with the cellulase preparation according to any one of (1) to (3).
(13) A method for producing a sugar from biomass, the method comprising the step of bringing a cellulose-containing biomass into contact with the cellulase preparation according to any one of (1) to (3).

Advantageous Effects of Invention

The present invention provides a cellulase preparation exhibiting a high activity and an activity in a wide pH range. Moreover, the present invention provides a method for easily producing such a cellulase preparation. The use of the cellulase preparation obtained according to the present invention enables, for example, efficient improvement in touch feel and appearance of a cellulose-containing fiber and saccharification of biomass.

DESCRIPTION OF EMBODIMENTS

Cellulase Preparation

In the present invention, a cellulase refers to an enzyme having an activity of breaking down cellulose, and a cellulase preparation refers to a preparation comprising cellulase components such as cellobiohydrolases, endoglucanases, and β-glucosidase.

The cellulase preparation of the present invention is characterized by comprising endoglucanases derived from two different types of microorganisms. The two different types of microorganisms from which the endoglucanases are derived are preferably two different types of filamentous fungi. Examples of the filamentous fungi include those belonging to genera *Trichoderma, Penicillium, Staphylotrichum, Humicola, Acremonium, Aspergillus, Rizopus, Mucor,* and *Phycomyces*. Preferable examples thereof include *Trichoderma viride, Penicillium pinophilum, Staphylotrichum cocosporum, Humicola insolens, Acremonium cellulolyticus, Aspergillus niger, Aspergillus aculeatus, Rizopus oryzae, Mucor circinelloides,* and *Phycomyces nitens*.

Preferably, two main types of the endoglucanases comprised in the cellulase preparation of the present invention are derived from different microorganisms, and are selected from endoglucanases classified in different GH families. Herein, the "main endoglucanase" refers to an endoglucanase having the highest protein weight among the endoglucanases comprised in the cellulase preparation. Thus, the "two main types of the endoglucanases" refer to an endoglucanase having the highest protein weight and an endoglucanase having the second highest protein weight among the endoglucanases comprised in the cellulase preparation. The protein weight can be calculated as follows. Specifically, SDS-PAGE is carried out on the cellulase preparation, and the concentration (protein amount) of each protein band in a migrating image is analyzed by densitometry. Note that a certain endoglucanase includes one that is broken down and one that is not broken down. Accordingly, in the analysis on a migrating image of SDS-PAGE, a translated product of the same endoglucanase gene may be observed as an irrelevant band. In the present invention, even if irrelevant bands are detected in a migrating image of SDS-PAGE, in a case where the translated products come from the same endoglucanase gene, these are evaluated as the endoglucanase of the same type, and the protein weight is calculated accordingly.

Each of the endoglucanases classified in the different GH families are desirably selected from endoglucanases classified in any of GH family 5, GH family 12, and GH family 45. Herein, "GH family" is a classification based on the primary structure of a glycoside hydrolase. Specifically, the endoglucanases are classified by a method described in the WEB page of CAZY (http://www.cazy.org/fam/accGH.html).

An example of the endoglucanase classified in GH family 5 is SCE3 derived from *Trichoderma viride*. In this respect, a naturally-occurring protein typical of "SCE3" is represented by an amino acid sequence of SEQ ID NO: 2. In the present invention, nevertheless, the protein may have the amino acid sequence of SEQ ID NO: 2 in which one or more amino acids are deleted, substituted, inserted, or added, as long as the endoglucanase activity is exhibited.

Moreover, an example of the endoglucanase classified in GH family 12 is PPCE derived from *Penicillium pinophilum*. In this respect, a naturally-occurring protein typical of "PPCE" is represented by an amino acid sequence of SEQ ID NO: 4. In the present invention, nevertheless, the protein may have the amino acid sequence of SEQ ID NO: 4 in which one or more amino acids are deleted, substituted, inserted, or added, as long as the endoglucanase activity is exhibited.

Further, an example of the endoglucanase classified in GH family 45 is STCE derived from *Staphylotrichum cocosporum*. In this respect, a naturally-occurring protein typical of "STCE" is represented by an amino acid sequence of SEQ ID NO: 6. In the present invention, nevertheless, the protein may have the amino acid sequence of SEQ ID NO: 6 in which one or more amino acids are deleted, substituted, inserted, or added, as long as the endoglucanase activity is exhibited.

The "one or more amino acids" modified in the endoglucanase are normally 50 amino acids or less, preferably 30 amino acids or less, and further preferably 10 amino acids or less (for example, 5 amino acids or less, or 3 amino acids or less). In a case where a certain amino acid of the endoglucanase is substituted with another amino acid, the substitution is preferably a substitution between amino acids having similar properties (conservative substitution) so that the endoglucanase activity can be maintained.

In the present invention, a combination of the two main types of the endoglucanases comprised in the cellulase preparation is particularly preferably a combination of SCE3 with PPCE or a combination of PPCE with STCE.

For example, the combination of SCE3 with PPCE can exhibit a surprisingly high fuzz-removing activity. The relative activity with respect to total cellulase amounts is approximately 2.4 to 3.0 times as high as a case where each endoglucanase is expressed alone. In addition to such a significant synergy effect, the pH property of the cellulase preparation obtained with this combination exhibits a wider profile than the case where each endoglucanase is expressed alone. Particularly, even if the pH is higher than 4, a high fuzz-removing activity at a level equivalent to a case of the optimum pH can be obtained in a certain pH range. For example, in a case where SCE3 is expressed alone, the fuzz-removing activity at pH 5 is approximately 75% of that at the optimum pH. In a case where PPCE is expressed alone, the fuzz-removing activity at pH5 is approximately 30% of that at the optimum pH. In a case where the two are combined, an equivalent activity to the fuzz-removing activity at the optimum pH can be exhibited even at pH 5. Herein, the "equivalent activity" means an activity of at least 90% or higher, preferably 95% or higher, and most preferably 100%. As described above, the combination of SCE3 with PPCE is characterized also by exhibiting the advantageous properties that cannot be expected from the pH property of each endoglucanase alone.

Additionally, for example, the combination of PPCE with STCE can exhibit a high fuzz-removing activity. The relative activity with respect to total cellulase amounts is approximately 3.2 to 3.7 times as high as a case where each endoglucanase is expressed alone. In addition to such a significant synergy effect, the pH property of the cellulase preparation obtained with this combination exhibits a wider profile than the case where each endoglucanase is expressed alone.

The cellulase preparation of the present invention comprising the two main types of the endoglucanases has a relatively high activity and a modified pH property in comparison with the case where each endoglucanase is expressed alone.

To increase the activity of the cellulase preparation in an absolute sense, the cellulase preparation comprises the two main types of the endoglucanases in an amount of at least 10% by weight (of total cellulases), further preferably at least 20% by weight. For the combination of SCE3 with PPCE, the cellulase preparation may comprise SCE3 in an amount of at least 40o by weight and PPCE in an amount of at least 20% by weight, for example. Moreover, for the combination of PPCE with STCE, the cellulase preparation may comprise PPCE in an amount of at least 15% by weight and STCE in an amount of at least 25% by weight, for example Herein, the "total cellulases" refer to a total weight of cellobiohydrolases, endoglucanases, and β-glucosidase comprised in the cellulase preparation. For example, in a case where an endoglucanase is expressed as a recombinant protein in *Trichoderma viride* strain 2 as a host, the amount of the total cellulases is the total weight of CBH1 and CBH2 as the cellobiohydrolases, EG1, SCE3, and endoglucanase (GH family 74) as the endoglucanases, and BGL as the β-glucosidase derived from the host in addition to the recombinant endoglucanase.

DNAs Encoding Endoglucanases and Acquisition thereof

In the present invention, a DNA encoding an endoglucanase refers to a DNA encoding the amino acid sequence of the above-described endoglucanase.

In the present invention, the DNA encoding the endoglucanase can be obtained artificially by chemical synthesis based on a base sequence of an endoglucanase gene or the amino acid sequence of the endoglucanase. Moreover, the DNA encoding the endoglucanase of the present invention can be amplified, using a primer synthesized based on a base sequence of a known endoglucanase gene or an amino acid sequence of a known endoglucanase, by PCR with a template of a DNA containing the gene, such as genomic DNA, cDNA, and plasmid. Further, the DNA encoding the endoglucanase of the present invention can also be obtained, using a gene fragment of the endoglucanase, as a probe, synthesized based on a base sequence of a known endoglucanase gene or an amino acid sequence of the known endoglucanase, by screening a genomic DNA library or cDNA library containing the endoglucanase gene for positive clones containing the endoglucanase gene.

In addition, to express the DNA encoding the endoglucanase to be introduced in a host cell as the endoglucanase having an activity, the DNA encoding the endoglucanase preferably contains, for example, a base sequence for regulating the expression or a genetic marker for selecting a transformant. Examples of the base sequence for regulating the expression include base sequences encoding a promoter, terminator, and signal peptide; and the like. The promoter is not particularly limited, as long as the transcriptional activity is exhibited in the host cell. The promoter can be obtained as a base sequence for regulating the expression of a gene encoding a protein that is either homologous or heterologous to the host cell. Moreover, the signal peptide is not particularly limited, as long as the signal peptide contributes to secretion of the protein in the host cell. The signal peptide can be obtained from a base sequence derived from the gene encoding the protein that is either homologous or heterologous to the host cell.

Host Cell and Transformation thereof

As the host cell into which the DNA encoding the endoglucanase is introduced in the present invention, *E. coli*, Actinomycetes, yeasts, filamentous fungi, and the like can be utilized. Filamentous fungi excellent in protein productivity are preferably used. Moreover, as the filamentous fungi used as the host cell, those belonging to genera *Humicola, Aspergillus, Trichoderma, Fusarium, Acremonium,* and *Penicillium* can be utilized. Furthermore, preferable examples thereof include *Humicola insolens, Aspergilluss niger, Aspergillus oryzae, Trichodermaviride, Fusarium oxysporum, Acremonium cellulolyticus,* and *Penicillium pinophilum.*

In the present invention, the DNA encoding the endoglucanase can be introduced into the host cell by a method in which the DNA encoding the endoglucanase is directly introduced, as well as a method in which the host cell is transformed with an expression vector which is replicable in the host cell and which contains a gene encoding the cellulase in an expressable state. The expression vector used for the transformation of the host cell can be constructed based on a self-replicating vector, i.e., for example, a plasmid which exists as an extrachromosomal element, and which replicates independently of the replication of the chromosome. Alternatively, the expression vector may be replicated together with the chromosome of the host microorganism, after introduced into the host microorganism and incorporated into the genome thereof. As a procedure and a method for constructing the vector according to the present invention, any procedure and any method commonly used in the field of genetic engineering can be used.

In the present invention, the transformation of the host cell with the DNA encoding the endoglucanase and the expression vector can be carried out according to any method commonly used in this field. The method of introducing the DNA encoding the endoglucanase into the host cell is carried out by introducing DNAs encoding two types of the endoglucanases or expression vectors containing these into the host cell simultaneously. Alternatively, the two types of the cellulase genes or the expression vectors containing these may be introduced into the host cell in a stepwise manner; specifically, one of the DNAs encoding the endoglucanases to be introduced or one of the expression vectors containing these is first introduced into the host cell, and subsequently, the other of the DNAs encoding the endoglucanases or the other of the expression vectors is introduced in a resultant transformant. Beside, a genetic marker used in the transformation may be selected as appropriate according to the method of selecting the transformant. For example, a gene encoding drug resistance or a gene complementing the auxotrophy can be used.

Production of Cellulase Preparation

The cellulase preparation of the present invention can be produced as follows. Specifically, the above-described transformed host cell is cultured in an appropriate medium, and recombinant cellulases are obtained from the resultant culture. The culturing and conditions for the host cell expressing the two types of the recombinant endoglucanases may be substantially the same as those for the host cell used.

Uses of Cellulase

In the present invention, when a cellulose-containing fiber is treated with the cellulase preparation or a cellulase agent utilizing the same, a cellulose-containing fiber having improved touch feel and appearance can be produced. It is also possible to give a colored cellulose-containing fiber a "stonewashed" appearance providing local variations in color.

Furthermore, according to the present invention, when biomasses, such as rice straw, bagasse, corn stover, pomace of a fruit such as a palm seed, and waste wood, are treated with the recombinant cellulase preparation or the cellulase agent utilizing the same, a sugar can be produced (saccharification) from these biomasses. The sugar obtained in this manner can be further converted into ethanol by fermentation with a yeast or the like.

EXAMPLES

The present invention will be more specifically described by way of Examples, but the present invention is not to be limited to Examples below but is still within the gist of the present invention.

Example 1

Preparing of *Trichoderma viride* Co-Expressing Endoglucanase SCE3 and Endoglucanase PPCE (1) Construction of SCE3-Expression Plasmid pCB1-sce3

As an expression vector for the endoglucanase SCE3 derived from *Trichoderma viride*, pCB1-sce3 was used which was obtained by self-ligation of a fragment of approximately 7 kb obtained by digesting pCB1-Eg3X described in International Publication No. WO98/11239 with XbaI.

(2) Construction of PPCE-Expression Plasmid pPPCE-M

As an expression vector for the endoglucanase PPCE derived from *Penicillium pinophilum*, pPPCE-M described in WO 2008/11613 was used.

(3) Construction of Selection Marker-Expression Plasmid pPYR4

As a marker plasmid containing a pyr4 gene derived from *Neurospora crassa*, pPYR4 described in International Publication No. WO2005/056787 was used.

(4) Construction of Selection Marker-Expression Plasmid pDT-118

A plasmid pDT-118 was constructed by inserting, into an XbaI site of pUC118 (manufactured by TAKARA SHUZO CO., LTD.), a destomycin resistance gene (DtR) derived from *Streptomyces rimofacience* having a promoter and a terminator of an *Aspergillus nidulans*-derived trpC gene excised from pMKD01described in International Publication No. WO98/03667 with XbaI.

(5) Creation and Culturing of SCE3 alone-expressing strain

Transformation of *Trichoderma viride* with the plasmid pCB1-sce3 obtained in Example 1—(1) and the plasmid pPYR4 obtained in Example 1—(3) was carried out in accordance with the method described in WO 2005/056787. Specifically, this transformation was carried out by a co-transformation method using *Trichoderma viride* strain 2 deficient in a gene for uracil biosynthesis (pyr4) as a host and a pyr4 gene of *Neurospora crassa* as a selection marker. First, in accordance with the method described in WO 2005/056787, protoplasts of *Trichoderma viride* strain 2 were prepared, and 100 µL of the protoplast suspension thus obtained was mixed with 7 µg of pCB1-sce3 and 3 µg of pPYR4. After the liquid mixture was allowed to stand on ice for 5 minutes, 400 µL of a PEG solution (60% polyethylene glycol 4000, 10 mM calcium chloride, and 10 mM Tris-HCl buffer, pH 7.5) was added to the mixture, which was further allowed to stand on ice for 20 minutes. The protoplast suspension thus treated was washed with an SUTC buffer (0.5 M sucrose, 10 mM calcium chloride, and 10 mM Tris-HCl buffer, pH 7.5), and then overlaid with soft agar on a minimum medium containing 0.5 M of sucrose, followed by culturing at 28° C. for 5 days. After the culturing, grown colonies were again transferred on a minimum medium, and colonies grown on this medium was used as transformants. From the obtained transformants, 200 strains were inoculated into a PSW medium (1.0% glucose, 4.0% lactose, 2.0% soybean cake, 1.0% wheat germ, 0.2% potassium dihydrogen phosphate, 0.2% ammonium sulfate, 0.2% ammonium phosphate, and 0.2% calcium carbonate), and cultured at 28° C. for 5 days. After the culturing, mycelia were removed by centrifugation to obtain culture supernatants as crude enzyme solutions. The crude enzyme solutions were subjected to SDS-PAGE. This SDS-PAGE was carried out using an electrophoresis apparatus Safety Cell Mini STC-808 (manufactured by TEFCO) and Precast Mini Gel 12%-SDS-PAGE mini, 1.0 mm in gel thickness (manufactured by TEFCO). The electrophoresis method was carried out in accordance with protocols attached to the products. LMW Calibration For SDS Electrophoresis (manufactured by GE Healthcare Bio-Sciences) was used as a molecular weight marker. After the electrophoresis, in accordance with protocols attached thereto, Coomassie Brilliant Blue R250 (manufactured by NACALAI TESQUE, INC.) was used for staining, followed by decolorization. As a result, a protein of 45 kDa was expressed specifically in the transformants. Strain 2-99 having a particularly high expression amount was designated as a SCE3 alone-expressing strain.

(6) Creation and Culturing of SCE3·PPCE Co-Expressing strain

The SCE3 alone-expressing strain obtained in Example 1—(5) was transformed with pPPCE-M obtained in Example 1—(2) and pDt-118 obtained in Example 1—(4). The transformation method followed the method in Example 1—(5), and this transformation was carried out by a co-transformation method using the SCE3 alone-expressing strain as a host and the destomycin resistance gene (DtR) as a selection marker. The SCE3 alone-expressing strain was transformed using 7 μg of pPPCE-M and 3 μg of pDt-118, and overlaid with PDA agar on a PDA medium containing 20 μg/ml hygrpmycin B, followed by culturing at 28° C. for 5 days. After the culturing, grown colonies were again transferred on a PDA medium containing hygrpmycin B, and colonies grown on this medium was used as transformants. Thus, 70 strains of the transformants were obtained. From the obtained transformants, the 70 strains were inoculated into a PSW medium described in Example 1—(5), and cultured at 28° C. for 5 days. After the culturing, mycelia were removed by centrifugation to obtain culture supernatants as crude enzyme solutions. The crude enzyme solutions were subjected to SDS-PAGE, and a protein of approximately 26 kDa was specifically expressed in the transformants. Strain 11-8 having a particularly high expression amount was designated as a SCE3·PPCE co-expressing strain.

(7) Creation and Culturing of PPCE Alone-Expressing strain

Transformation of Trichoderma viride strain 2 with pPPCE-M obtained in Example 1—(2) and pPYR4 obtained in Example 1—(3) was carried out in accordance with the method described in Example 1—(5). Specifically, Trichoderma viride strain 2 was transformed using 7 μg of pPPCE-M and 3 μg of pPYR4, and overlaid with soft agar on a minimum medium, followed by culturing at 28° C. for 5 days. After the culturing, grown colonies were again transferred on a minimum medium, and colonies grown on this medium were used as transformants. The obtained transformants were cultured by the method described in Example 1—(5). The strain which expressed a significant amount of PPCE was designated as a PPCE alone-expressing strain.

(8) Measurement of Expressed Protein Concentration

The SCE3 alone-expressing strain, the PPCE alone-expressing strain, and the SCE3·PPCE co-expressing strain were evaluated in terms of the amount of recombinant endoglucanase expressed. The total protein amount of each of the culture supernatants was measured using BIO-RAD Protein Assay Kit (manufactured by Bio-Rad Inc.) in accordance with protocols attached thereto. Subsequently, electrophoresis was carried out on the culture supernatant in an amount of 11 ·g as the protein amount by the method described in Example 1—(5). Bands were analyzed using Molecular Imager FX (manufactured by Bio-Rad Laboratories, Inc.) and Quantity One (manufactured by Bio-Rad Laboratories, Inc.) to determine a ratio of the expressed cellulase to the total cellulase components. Here, the conditions for the band analysis were: sensitivity of 7.513 and rolling disk size of 10. Table 1 shows the result. From this result, in the SCE3·PPCE co-expressing strain, SCE3 and PPCE were two main types of the endoglucanases, and the ratios to the total cellulases were respectively 40.8% and 20.2%.

Additionally, as shown in Table 1, in the case where both SCE3 and PPCE were simultaneously expressed, a culture supernatant having a higher recombinant endoglucanase ratio was obtained than the case where each endoglucanase was expressed alone.

TABLE 1

Ratios of protein components in *Trichoderma viride* strain 2 recombinants

|  | SCE3 alone-expressing strain | PPCE alone-expressing strain | SCE3 · PPCE co-expressing strain |
|---|---|---|---|
| Endoglucanase (GH family 74) | 0.7% | 1.6% | 0.5% |
| BGL | 2.7% | 2.8% | 1.8% |
| CBH1 | 16.9% | 21.4% | 15.4% |
| CBH2 | 6.2% | 12.8% | 3.9% |
| EG1 | — | 4.5% | — |
| SCE3 | 44.9% | 6.0% | 40.8% |
| PPCE | 0% | 29.8% | 20.2% |
| Recombinant endoglucanase ratio | 44.9% | 29.8% | 61.0% |

Example 2

Comparison of Fuzz-Removing Activities Among SCE3 Alone-Expressing Strain, PPCE Alone-Expressing Strain, and SCE3·PPCE Co-Expressing Strain The culture supernatants of the SCE3 alone-expressing strain, the PPCE alone-expressing strain, and the SCE3·PPCE co-expressing strain prepared in Example 1 were used to examine the fuzz-removing activities under the following washing conditions.

<Conditions>

Testing machine: Launder Meter L-12 (manufactured by DAIEI KAGAKU SEIKI MFG. CO., LTD.)

Temperature: 40° C.

Time: 60 minutes

Reaction solution: 5 mmol/L acetic acid buffer (pH 4) 40 ml

To a treating solution, an appropriate amount of rubber balls were added together with each culture supernatant.

After washing, extents of fuzz removed were judged visually, and the amounts of culture supernatants required to remove approximately 50% of fuzz on the basis of a visual evaluation were calculated. Relative activities were determined from the liquid amounts, where the fuzz-removing activity of the culture supernatant of the PPCE alone-expressing strain was regarded as 100%. In addition, from the result of Example 1, the total cellulase weights in the culture supernatants were calculated, and relative fuzz-removing activities with respect to the total cellulase amounts were calculated. As a result, as shown in Table 2, the SCE3·PPCE co-expressing strain containing both recombinant endoglucanases of SCE3 and PPCE exhibited activities 4.1 times as high as the PPCE alone-expressing strain with respect to the culture supernatant, and 2.4 times with respect to the total cellulases. Further, the SCE3·PPCE co-expressing strain exhibited activities 5.1 times as high as the SCE3 alone-expressing strain with respect to the culture supernatant, and 3 times with respect to the total cellulases.

The results above showed that in the case where SCE3 and PPCE were co-expressed, a synergistically high fuzz-removing activity was obtained in comparison with the case where each endoglucanase was expressed alone.

TABLE 2

Comparison of fuzz-removing activities among SCE3 alone-expressing strain, PPCE alone-expressing strain, and SCE3 · PPCE co-expressing strain

| Enzyme | Relative activity with respect to culture supernatant (%) | Relative activity with respect to total cellulases (%) |
| --- | --- | --- |
| SCE3 alone-expressing strain | 80 | 80 |
| PPCE alone-expressing strain | 100 | 100 |
| SCE3 · PPCE co-expressing strain | 410 | 240 |

Example 3

Figure 1:
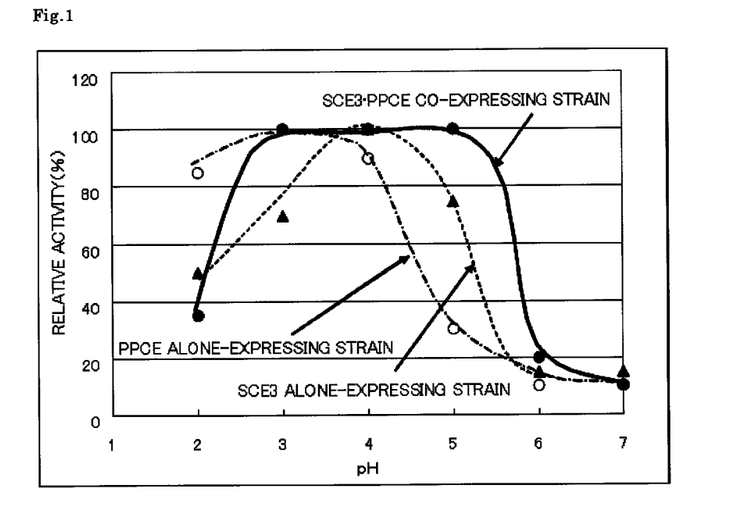
FIG. 1 is a graph showing the result of analyzing pH properties in the fuzz-removing activities of a SCE3 alone-expressing strain, a PPCE alone-expressing strain, and a SCE3·PPCE co-expressing strain.

Analysis of pH Properties in Fuzz-Removing Activities of SCE3 Alone-Expressing Strain, PPCE Alone-Expressing Strain, and SCE3·PPCE Co-Expressing Strain The culture supernatants of the SCE3 alone-expressing strain, the PPCE alone-expressing strain, and the SCE3·PPCE co-expressing strain used in Example 1 was used to investigate the pH property of each enzyme in accordance with the method described in Example 2. Consequently, results as shown in Table 3 and FIG. 1 were obtained. The SCE3·PPCE co-expressing strain exhibited a wider pH profile where the high activity was maintained from weak acid to acid than the alone-expressing strains. In particular, surprisingly, in the case where SCE3 was expressed alone, the fuzz-removing activity at pH 5 was approximately 75% of that at the optimum pH. In the case where PPCE was expressed alone, the fuzz-removing activity at pH 5 was approximately 30% of that at the optimum pH. Meanwhile, in the case where the two were combined, the fuzz-removing activity at pH 5 was exhibited to be equivalent to the activity at the optimum pH.

TABLE 3 pH profile of each culture supernatant

| Buffer, pH | Relative activity of SCE3 alone-expressing strain (%) | Relative activity of PPCE alone-expressing strain (%) | Relative activity of SCE3 · PPCE co-expressing strain (%) |
| --- | --- | --- | --- |
| citric acid, pH 2 | 50 | 85 | 35 |
| acetic acid, pH 3 | 70 | 100 | 100 |
| acetic acid, pH 4 | 100 | 90 | 100 |
| acetic acid, pH 5 | 75 | 30 | 100 |
| acetic acid, pH 6 | 15 | 10 or less | 20 |
| Phosphoric acid, pH 7 | 15 | 10 or less | 10 or less |

Example 4

Preparing of *Trichoderma Viride* Co-Expressing Endoglucanase STCE and Endoglucanase PPCE (1) Construction of STCE-Expression pCB-Stm12

As an expression vector for the endoglucanase STCE derived from *Staphylotrichum cocosporum*, pCB-Stm12 described in Example B4 of WO 2005/056787 was used.

(2) Creation of STCE Alone-Expressing strain

Transformation of *Trichoderma viride* with the plasmid pCB-stm12 and the plasmid pPYR4 and culturing of the transformants were carried out by the same method as described in Example 1—(5). The method described in WO 2005/056787 was followed. From the obtained transformants of 80 strains, crude enzyme solutions were prepared, and subjected to SDS-PAGE in accordance with Example 1—(5). As a result, a protein of 45 kD was expressed specifically in the transformants. Strain m12-60 having a particularly high expression amount was designated as a STCE alone-expressing strain.

(3) Creation of STCE·PPCE Co-Expressing strain

The STCE alone-expressing strain created in Example 4—(2) was transformed with pPPCE-M obtained in Example 1—(2) and pDT-118 obtained in Example 1—(4). As the transformation method, this trans format ion was carried out in accordance with the method in Example 1—(5). From the obtained transformants, 70 strains were cultured by the method described in Example 1—(5), and crude enzyme solutions were prepared. The crude enzyme solutions were subjected to SDS-PAGE, and a protein of approximately 26 kD was expressed specifically in the transformants. Strain 10-82 having a particularly high expression amount was designated as a STCE·PPCE co-expressing strain.

(4) Measurement of Expressed Protein Concentration

By the method described in Example 1—(8), the STCE alone-expressing strain, the PPCE alone-expressing strain, and the STCE·PPCE co-expressing strain were evaluated in terms of the amount of cellulase component expressed. Table 4 shows the result. From this result, in the STCE·PPCE co-expressing strain, STCE and PPCE were two main types of the endoglucanases, and the ratios to the total cellulases were respectively 25.5% and 18.5%. Additionally, in the case where both STCE and PPCE were simultaneously expressed, a culture supernatant having a higher recombinant endoglucanase ratio was obtained than the case where each endoglucanase was expressed alone.

TABLE 4

Ratios of protein components in *Trichoderma viride* strain 2 recombinants

| | STCE alone-expressing strain | PPCE alone-expressing strain | STCE · PPCE co-expressing strain |
|---|---|---|---|
| Endoglucanase (GH family 74) | 1.3% | 1.6% | 1.7% |
| BGL | 4.3% | 2.8% | 3.1% |
| CBH1 | 19.8% | 21.4% | 14.5% |
| CBH2 | 14.4% | 12.8% | 7.4% |
| EG1 | 5.5% | 4.5% | 4.6% |
| SCE3 | 5.1% | 6.0% | 4.1% |
| STCE | 36.4% | 0% | 25.5% |
| PPCE | 0% | 29.8% | 18.5% |
| Recombinant endoglucanase ratio | 36.4% | 29.8% | 44.0% |

Example 5

Comparison of Fuzz-Removing Activities Among STCE Alone-Expressing Strain, PPCE Alone-Expressing Strain, and STCE·PPCE Co-Expressing Strain The culture supernatants of the STCE alone-expressing strain, the PPCE alone-expressing strain, and the STCE·PPCE co-expressing strain prepared in Examples 1 and 4 were used to investigate the fuzz-removing activities by the same method as in Example 2. In addition, from the result of Example 4, the total cellulase weights in the culture supernatants were calculated, and relative fuzz-removing activities with respect to the total cellulase amounts were calculated. As a result, as shown in Table 5, the STCE·PPCE co-expressing strain containing both recombinant endoglucanases of STCE and PPCE exhibited activities 4.2 times as high as the PPCE alone-expressing strain with respect to the culture supernatant, and 3.7 times with respect to the total cellulases. Further, the STCE·PPCE co-expressing strain exhibited activities 3.5 times as high as the STCE alone-expressing strain with respect to the culture supernatant, and 3.2 times with respect to the total cellulases.

The results above showed that in the case where STCE and PPCE were co-expressed, a synergistically high fuzz-removing activity was obtained in comparison with the case where each endoglucanase was expressed alone.

TABLE 5

Comparison of fuzz-removing activities among STCE alone-expressing strain, PPCE alone-expressing strain, and STCE · PPCE co-expressing strain

| Enzyme | Relative activity with respect to culture supernatant (%) | Relative activity with respect to total cellulases (%) |
|---|---|---|
| STCE alone-expressing strain | 120 | 115 |
| PPCE alone-expressing strain | 100 | 100 |
| STCE · PPCE co-expressing strain | 420 | 370 |

Example 6

Figure 2:
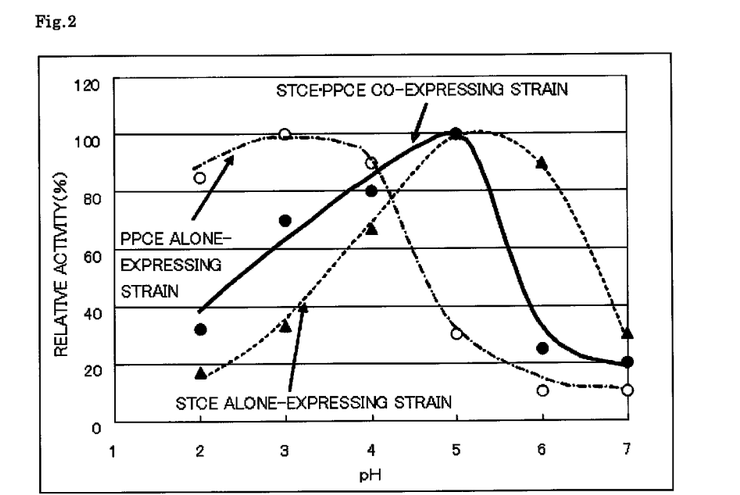
FIG. 2 is a graph showing the result of analyzing pH properties in the fuzz-removing activities of a STCE alone-expressing strain, the PPCE alone-expressing strain, and a STCE·PPCE co-expressing strain.

Analysis of pH Properties in Fuzz-Removing Activities of STCE Alone-Expressing Strain, PPCE Alone-Expressing Strain, and STCE·PPCE Co-Expressing Strain The culture supernatants of the STCE alone-expressing strain, the PPCE alone-expressing strain, and the STCE·PPCE co-expressing strain prepared in Examples 1 and 4 were used to examine the pH profile by the same method as in Example 3 under the following washing conditions. Consequently, results as shown in Table 6 and FIG. 2 were obtained. The STCE·PPCE co-expressing strain exhibited a wider pH profile where the high activity was maintained from weak acid to acid than the alone-expressing strains.

TABLE 6 pH profile of each culture supernatant

| Buffer, pH | Relative activity of STCE alone-expressing strain (%) | Relative activity of PPCE alone-expressing strain (%) | Relative activity of STCE · PPCE co-expressing strain (%) |
|---|---|---|---|
| citric acid, pH 2 | 17 | 85 | 32 |
| acetic acid, pH 3 | 33 | 100 | 70 |
| acetic acid, pH 4 | 67 | 90 | 80 |
| acetic acid, pH 5 | 100 | 30 | 100 |
| acetic acid, pH 6 | 90 | 10 or less | 25 |
| phosphoric acid, pH 7 | 63 | 10 or less | 20 |

[INDUSTRIAL APPLICABILITY]

A cellulase preparation of the present invention has a high activity and a wide pH property. The cellulase preparation of the present invention is utilizable in production of a cellulose-containing fiber having improved touch feel and appearance and in formation of a "stonewashed" appearance of a colored cellulose-containing fiber. Moreover, the cellulase preparation of the present invention is also utilizable in production of a sugar (saccharification) from a biomass such as rice straw, bagasse, corn stover, pomace of a fruit such as a palm seed, and waste wood, and eventually, in production of bioethanol.

The invention claimed is:

1. A cellulase preparation comprising at least two different isolated endoglucanases, wherein the two different endoglucanases are: (a) an endoglucanase classified in GH family 5, and an endoglucanase classified in GH family 12; or (b) an endoglucanase classified in GH family 12, and an endoglucanase classified in GH family 45, wherein
the endoglucanase classified in GH family 5 comprises the amino acid sequence of SEQ ID NO: 2, or comprises the amino acid sequence of SEQ ID NO: 2 but in which ten or less amino acids are deleted, substituted, inserted, or added;
the endoglucanase classified in GH family 12 comprises the amino acid sequence of SEQ ID NO: 4, or comprises the amino acid sequence of SEQ ID NO: 4 but in which ten or less amino acids are deleted, substituted, inserted, or added; and
the endoglucanase classified in GH family 45 comprises the amino acid sequence of SEQ ID NO: 6, or comprises the amino acid sequence of SEQ ID NO: 6 but in which ten or less amino acids are deleted, substituted, inserted, or added, and wherein the preparation exhibits synergistic fuzz-removing activity.

2. The cellulase preparation according to claim 1, wherein two main types of the endoglucanases are each contained in an amount of at least 10% by weight of total cellulases.

3. The cellulase preparation according to claim 2, wherein the two main types of the endoglucanases are each contained in an amount of at least 20% by weight of the total cellulases.

4. A method for producing the cellulase preparation according to claim 1, said method comprising the step of culturing a transformant which contains DNAs encoding the two different endoglucanases.

5. The method according to claim 4, wherein the host cell is a filamentous fungus.

6. A method for producing an improved cellulose-containing fiber, the method comprising the step of bringing a cellulose-containing fiber into contact with the cellulase preparation according to claim 1.

7. A method for producing a sugar from biomass, the method comprising the step of bringing a cellulose-containing biomass into contact with the cellulase preparation according to claim 1.

* * * * *